United States Patent
Goodyear et al.

(10) Patent No.: US 9,995,713 B2
(45) Date of Patent: Jun. 12, 2018

(54) APPARATUS FOR DETECTING FERROMAGNETIC OBJECTS AND SCREENING PEOPLE AND EQUIPMENT

(75) Inventors: Simon Wray Goodyear, Malvern (GB); Simon Edward James Collinge, Cranfield (GB); Mark Nicholas Keene, Malvern (GB)

(73) Assignee: Metrasens Limited, Malvern (GB)

( * ) Notice: Subject to any disclaimer, the term of this patent is extended or adjusted under 35 U.S.C. 154(b) by 872 days.

(21) Appl. No.: 14/129,877

(22) PCT Filed: Jun. 27, 2012

(86) PCT No.: PCT/GB2012/051500
§ 371 (c)(1),
(2), (4) Date: Mar. 31, 2014

(87) PCT Pub. No.: WO2013/001292
PCT Pub. Date: Jan. 3, 2013

(65) Prior Publication Data
US 2014/0232382 A1     Aug. 21, 2014

(30) Foreign Application Priority Data
Jun. 29, 2011 (GB) .................................. 1111067.3

(51) Int. Cl.
*G01N 27/72* (2006.01)
*G01R 33/12* (2006.01)
(Continued)

(52) U.S. Cl.
CPC .............. *G01N 27/72* (2013.01); *A61B 5/05* (2013.01); *G01V 3/08* (2013.01)

(58) Field of Classification Search
CPC ........... B29C 65/5057; B29C 65/8269; G01N 27/72; G01N 27/9033; G01N 27/87
(Continued)

(56) References Cited

U.S. PATENT DOCUMENTS 4,024,468 A * 5/1977 Hirschi .................. G01V 3/107
324/243
4,249,128 A * 2/1981 Karbowski ............ G01V 3/105
324/329
(Continued)

FOREIGN PATENT DOCUMENTS

GB        2 395 276 A       5/2004
WO     20081028487 A1       3/2008

OTHER PUBLICATIONS

International Search Report and Written Opinion dated May 14, 2013, issued in corresponding International Application No. PCT/GB2012/051500, filed Jun. 27, 2012, 9 pages.
(Continued)

*Primary Examiner* — Giovanni Astacio-Oquendo
(74) *Attorney, Agent, or Firm* — Christensen O'Connor Johnson Kindness PLLC

(57) ABSTRACT

Apparatus for detecting a ferromagnetic object located on or in a person being screened comprises a first magnetic sensor which in use measures an ambient magnetic field or gradient within a first volume of space and produces a corresponding measurement signal, a primary power supply which provides power to the magnetic sensor, a signal processing circuit arranged in communication with the magnetic sensors configured to identify temporal variations in the measurement signal and from the identified temporal variations provide an output signal indicative of the presence of a ferromagnetic object within the volume of space, and a warning device operable by the output from the signal processing circuit to provide within the vicinity the apparatus at least one of an audible and a visible warning in response to the output signal from the signal processing circuit. The apparatus include a user operable input means
(Continued)

which enables the warning device to be disabled by a user without powering down the magnetic sensors.

23 Claims, 5 Drawing Sheets

(51) Int. Cl.
*A61B 5/05* (2006.01)
*G01V 3/08* (2006.01)

(58) Field of Classification Search
USPC .......................... 324/239, 200, 228, 243, 329
See application file for complete search history.

(56) References Cited

U.S. PATENT DOCUMENTS

| | | | | |
|---|---|---|---|---|
| 4,334,191 | A * | 6/1982 | Podhrasky | G01V 3/105 |
| | | | | 324/329 |
| 4,488,115 | A | 12/1984 | Podhrasky | |
| 4,942,360 | A * | 7/1990 | Candy | G06K 9/3241 |
| | | | | 324/329 |
| 5,039,981 | A * | 8/1991 | Rodriguez | G08B 13/24 |
| | | | | 324/228 |
| 5,148,151 | A * | 9/1992 | Podhrasky | G01V 3/105 |
| | | | | 324/329 |
| 5,959,451 | A | 9/1999 | De Torfino | |
| 7,296,683 | B1 | 11/2007 | Vallelonga, Sr. | |
| 7,408,461 | B2 * | 8/2008 | Fluck | G01V 3/081 |
| | | | | 324/243 |
| 7,414,404 | B2 * | 8/2008 | Keene | G01V 3/107 |
| | | | | 324/243 |
| 7,893,690 | B2 * | 2/2011 | Simon | G01V 3/107 |
| | | | | 324/225 |
| 2003/0171669 | A1 | 9/2003 | Kopp | |
| 2004/0147833 | A1 | 7/2004 | Czipott | |
| 2005/0119547 | A1 * | 6/2005 | Shastri | A61B 5/164 |
| | | | | 600/407 |
| 2005/0242817 | A1 * | 11/2005 | Hoult | G01V 3/10 |
| | | | | 324/326 |
| 2006/0145691 | A1 | 7/2006 | Massengill | |
| 2006/0158331 | A1 | 7/2006 | Massengill | |
| 2007/0052411 | A1 | 3/2007 | McClure et al. | |
| 2012/0074943 | A1 * | 3/2012 | MacLeod | G01R 33/025 |
| | | | | 324/318 |
| 2013/0307533 | A1 * | 11/2013 | Keene | G01R 33/0047 |
| | | | | 324/244 |

OTHER PUBLICATIONS

United Kingdom Search Report dated Oct. 17, 2011, issued in corresponding British Application No. GB1111067.3, filed Jun. 29, 2011, 4 pages.

Communication Pursuant to Article 94(3) EPC dated Oct. 11, 2017, issued in corresponding European Application No. 12761755.3, filed Jun. 27, 2012, 7 pages.

* cited by examiner

APPARATUS FOR DETECTING FERROMAGNETIC OBJECTS AND SCREENING PEOPLE AND EQUIPMENT

The present invention relates to apparatus for detecting the presence of ferromagnetic objects on a person, in particular to apparatus for use in pre-screening of patients before they enter a room containing a magnetic resonance imagining (MRI) scanner. It also relates to a method of screening a patient.

In GB 2 395 276 there is taught an apparatus which is able to detect ferromagnetic objects by providing a primary sensor means comprising first and second passive magnetic sensors which detect the disturbances in the ambient magnetic field which occur as the object moves through the field. The apparatus also includes a secondary non-magnetic sensor means which detects movement of objects in the vicinity of the primary sensor means. If both the primary and secondary sensing means detect a moving object an alarm is triggered. It is proposed in that patent that the apparatus may be mounted to the wall on either side of a doorway to a room containing a magnetic resonance imaging apparatus, with the secondary sensor means being arranged to detect objects approaching or about to pass through the doorway. Because both the primary and secondary sensors must detect the object this arrangement helps to reduce false alarms.

The apparatus described above works very well to warn people who may be unintentionally about to take a ferromagnetic object into an MRI room. It is known that there have in the past been several unfortunate accidents which have occurred due to a ferrous object entering an MRI room and being magnetically propelled, at high velocity, into the MRI machine within the room. This is called the projectile effect, and is well described in GB 2 395 276.

Ideally, before a person attempts to enter a room containing an MRI machine they will have been screened for magnetic objects. This requires an MRI qualified person to carry out a screening procedure on the patient before they approach the room. Combined with the use of an optional detector at the door to the room, the risk of the person taking a magnetic object into the room is greatly reduced.

Furthermore, a patient may inadvertently be carrying ferromagnetic objects that are not substantial enough to be a projectile effect hazard. Such objects may cause degradation in the MRI image and require the patient to be re-scanned. This reduces the efficiency of the MRI scanning process in hospitals. Examples of objects in this category include hair/bobby pins, wrist-watches and jewellery clasps and pins.

According to a first aspect the invention provides apparatus for detecting a ferromagnetic object located on or in a person being screened, the apparatus comprising:

a first magnetic sensor which in use measures an ambient magnetic field or gradient within a first volume of space and produces a corresponding measurement signal, a primary power supply which provides power to the magnetic sensors, a signal processing circuit arranged in communication with the magnetic sensors configured to identify temporal variations in the measurement signal and from the identified temporal variations provide an output signal indicative of the presence of a ferromagnetic object within the first volume of space, and a warning device operable by the output from the signal processing circuit to provide within the vicinity the apparatus at least one of an audible and a visible warning in response to the output signal from the signal processing circuit, and characterised in that the apparatus include a user operable input means which enables the warning device to be disabled by a user without powering down the magnetic sensors.

Most preferably the apparatus also includes a second magnetic sensor which in use measures an ambient magnetic field or gradient within a second volume of space that at least partially overlaps the first volume of space and produces a corresponding measurement signal, and signal processing circuit is arranged in communication with the first and second magnetic sensors and is configured to identify temporal variations in the measurement signal and from the identified temporal variations provide an output signal indicative of the presence of a ferromagnetic object within the overlapping regions of the two volumes of space. This can be readily extended to three or four or more magnetic sensors.

By an overlapping region of two localised volumes of space we mean a space in a known region which is close to the apparatus, typically within 1 meter of the apparatus within which a person to be screened can be located. The space should be large enough to fully enclose a person of 99th percentile height or greater when standing by the apparatus, Each of the sensors may respond to ferromagnetic objects that are moving outside of the that space, but generally will be less sensitive for objects that are further away.

The signal processing circuit may include one or more filters and the output signals from the two sensors may be passed through the one or more filters, The filters may include a low pass filter, and may include a high pass filter. These may be combined in a band pass filter. The high pass filter may be configured to remove frequencies above, say, 10 Hz which typically correspond to changes in magnetic field caused by nearby electrical appliances. The low pass filter may be configure to remove frequencies below, say, 0.2 Hz, which mainly correspond to the background magnetic field produced by the earth which changes very slowly over time.

Where the output of the sensors is passed through a filter the user operable input means may enable the warning device to be disabled without powering down the filter. Such filters can take a long time to stabilise, so ensuring they are not powered down can reduce the time taken for the apparatus to be enabled when the user operable input means is operated. Disabling the warning device removes the unwanted feeling experienced by some MRI qualified personnel that they are constantly being monitored, and prevents false alarms being issued when they pass close to the apparatus with ferromagnetic objects during their day to day work when they are not in fact using the apparatus to screen a patient.

Operating the user operable input means may alter the value of a relatively low current electrical signal, the apparatus disabling or enabling the warning device according to the value of that signal. By relatively low current electrical signal we mean a signal of less than 1 mAmp such as a digital logic signal whereby the input means changes the logic level of the signal according to whether the user has enabled of disabled the warning device. By relatively low current we mean a current that is considerably lower than the current drawn by the signal processing means or warning device.

The signal may be carried from the user operable input device along twisted pair cables.

The applicant has appreciated that it is desirable to minimise the current flowing through cables to and from the input device because the changing signal may generate a magnetic flux which might be picked up by the sensors leading to false warning signals being generated. The lower the current the smaller the field and so the less likely this is to happen.

The apparatus may include a second power supply which provides at an output power for the warning device, the output of the power supply being switchable between a level at which the power to the warning device is enabled and a level at which power to the warning device is disabled, the condition of the output being dependent on the value of the signal from the user operable input means. For instance, the power supply may include a digital control circuit which may receive the signal from the user operable input means at an input terminal which causes the output of the power supply to switch on or off.

The second power supply may be switchable independently of the first power supply, ensuring that the power to the magnetic sensors and the filters (where present) is not interrupted.

The secondary power supply may be fed from a power output of the first power supply. Both the first power supply and the second power supply may comprise DC-DC converters and each may provide a dual polarity DC output signal, having a positive and negative output voltage, A third power supply may be provided. This may provide power to the first power supply and the second power supply where present. It may comprise a battery, or may comprise an AC-DC converter which may take an input from a mains supply and provide as an output a DC signal suitable for input to the other power supplies.

The output of the power supply (supplies) may be connected to the signal processing means and warning device through a twisted pair cable. This may comprise two conductive cables which are surrounded by respectively insulating sleeves and which are then twisted together along their length. Each conductive cable may in turn comprise two individual strands of conductive wire which are twisted together along their length within the insulating sleeves. The twisting helps to minimise the magnetic flux that is radiated from the cable towards the sensors, reducing or eliminating false warnings.

In an alternative to the user operable input means producing a relatively low level signal that is used to turn the output of a secondary power supply on or off, the user operable input means could comprise a switch that is arranged in series between at least one output of the first power supply, or second power supply where present, and the warning device. Therefore, rather than a low level signal the user device will interrupt the relatively higher current supply fed to the warning device. This, however, for the reasons already stated may not be preferred depending on the relative positions of the power supply and the user operable input means as it is desirable to minimise the amount of cable within the apparatus along which high currents travel, and clearly the power would need to run from the location of the power supply to the switch and then on to the warning device. In any event, even if the user operable input means and power supply are conveniently close together it is generally not desirable to tap into the output cables from the power supply as this can create unwanted localised magnetic fields that may cause false warnings.

The apparatus may comprise a single housing which may be pole shaped, and would normally be mounted on a wall when in use or optionally in a free standing base which supports the housing above the ground with the magnetic sensors being arranged within the housing. It may comprise a single housing, which may be elongate and may be shaped like a pole, which includes both the first and second magnetic sensors. The housing may define a single void within which the signal processing means, sensors and power supply (supplies) are provided but could define two or more voids which may be interconnected. The power supply (supplies), sensors, signal processing means and optionally the warning means may be located within the pole.

When in use (mounted on a wall or floor standing) the user operable input means may be located on the housing at a height where it can be pressed by a user of average height (between 5 and 6 foot tall) without having to stoop down, and the warning device may be located at the top of the housing.

The magnetic sensors may have an overlapping detection zone which lies to the front of the housing and encompasses a volume which extends from floor level up to at least 2.1 meters and outward from the housing by at least 1.2 meters. This defines a zone which will encompass the whole of a 99th percentile person standing in front of the housing, so that any ferromagnetic objects they are carrying, wearing or have inside their body will be detected by the signal processing means, The apparatus may include a mat which can be positioned on the ground in front of the housing and which indicates where a person must stand to be within the localised zone. The mat may carry indicia showing where the person should place their feet on the mat.

The user operable input means may be located at the front side of the housing. This allows a person standing in the sensitive zone to enable/disable the warning device in a convenient manner.

Where the housing comprises a pole, one of the magnetic sensors may be located at, or close to the top of the pole and the other one at or close to the bottom of the pole, and the input may be located conveniently at or close to the midpoint of the pole. They may be generally aligned with a vertical axis that passes through both sensors.

The user operable input means may comprise a button or a switch. It may comprise a non-contact type switch such as a proximity sensor, perhaps an optical sensor, which allows the switch to be operated without contact by a user.

The first and second sensors and the signal processing means may be configured as a gradiometer.

In one arrangement, the apparatus may include a third sensor and the first, second and third sensors may be configured as a second order gradiometer. The third sensor may be located towards the middle of the pole, midway between the first and second magnetic sensors. All three sensors may be aligned with a common vertical axis. The use of three sensors may provided an apparatus which is relatively more sensitive to nearby ferromagnetic objects and less sensitive to distant objects and which gives a larger change in output for a given movement of a nearby object. This is especially advantageous in a busy or compact environment where the potential for interfering magnetic fields from people and equipment moving nearby is high. In addition, it is also advantageous for an apparatus that may be temporarily located within a room, as less time has to be spent ensuring that it is positioned far enough away from potential interfering magnetic fields that could produce false warnings. With a less sensitive two sensor apparatus more care is needed during set up.

According to a second aspect the invention provides a method of screening a person or object comprising:

providing an apparatus comprising a first magnetic sensor which in use measures an ambient magnetic field or gradient within a first volume of space and produces a corresponding measurement signal, a primary power supply which provides power to the magnetic sensors, a signal processing circuit arranged in communication with the magnetic sensor configured to identify temporal variations in the measurement signal and from the identified temporal variations provide an output signal indicative of the presence of a ferromagnetic object within the volume of space, and a warning device operable by the output from the signal processing circuit to provide within the vicinity the apparatus at least one of an audible and a visible warning in response to the output signal from the signal processing circuit, the method comprising the steps of:

(a) Positioning the person or object to be screened within the volume of space in a first orientation, (b) Positioning the person or object in the volume of space in a second orientation which is at least 180 degrees out of alignment with the first position, and (c) Observing any warning from the warning device.

The method ensures that ferromagnetic items that are on a person or object being screened are always brought close to the sensors and as such only a single apparatus providing single-sided screening is required. This negates the need for having two apparatus forming a portal separated by enough distance for a person to pass through in order to scan both sides of the person.

The method may comprise a step of rotating the person or object through at least 180 degrees from the first orientation to a second orientation.

The step of rotating the person may comprise rotating them when they are positioned in the volume of space. It may rotate the patient through at least 360 degrees within that space. The apparatus may, at all times during the rotation, be switched on so that it is able to detect the presence of ferromagnetic objects about or in the patient.

The apparatus may include a user operable input which permits the warning device to be disabled without powering down the magnetic sensors and the method may comprise an additional step of enabling the display using the user operable input means. The apparatus may be in accordance with the first aspect of the invention.

Upon completion the method may comprise disabling the display without powering down the display using the user operable input means.

The method may include a step of introducing a magnetic object in front of the device after the display is powered up to test the display prior to position patient.

The method may include providing a mat and positioning the person on the mat, and rotating the person whilst the person is standing on the mat, the mat being positioned below the volume of space, and preferably wholly within the volume of space.

The method may comprise carrying the person in a non ferromagnetic portering means, such as a wheelchair, through the sensing volume of space of the apparatus first in one direction and then in the opposite direction in both cases close to the apparatus such that both sides of the person are scanned.

The method, although described in terms of screening a person, may equally be applied to the screening of an item of equipment by placing the equipment close to the apparatus and rotating it through 360 degrees.

There will now be described, by way of example only, one embodiment of the present invention with reference to the accompanying drawings of which:

Figure 1:
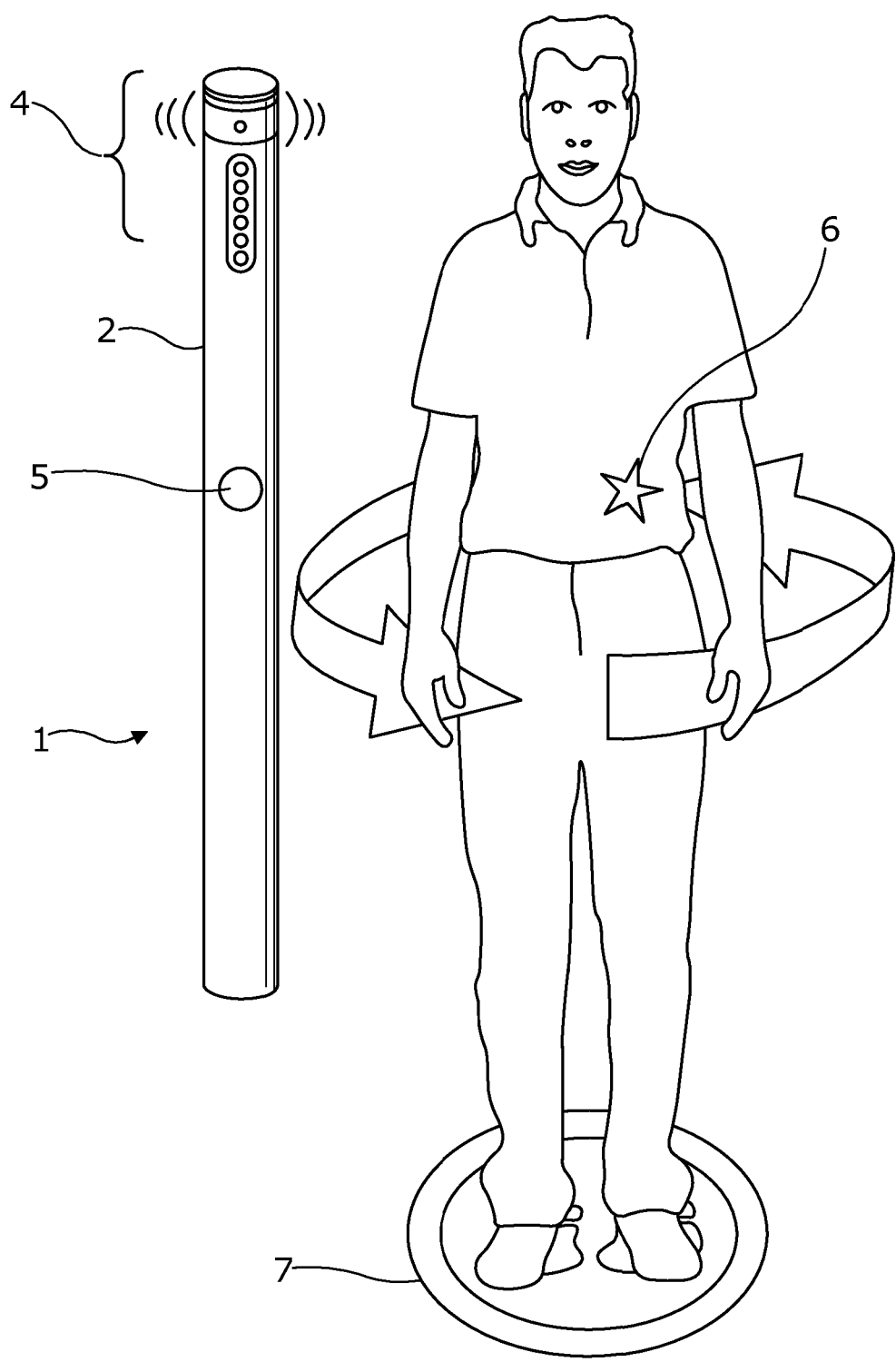
FIG. 1 is a general view of an embodiment of a screening apparatus in accordance with the invention.

Referring to FIG. 1, a screening apparatus 1 for use in pre-screening patients prior to their undergoing an MRI scan comprises an elongate pole shaped housing 2, about 1.5 meters in length which is secured to a wall. The housing 2 contains an electronic circuit as will be described in relation to FIGS. 2 and 3.

The electronic circuit includes a number of sensors which detect the presence of magnetic objects in close proximity to the housing. The top of the housing 2 includes a warning device 4 in the form of a visible. The display 4 comprises a beacon with a set of three coloured lights within a transparent housing, allowing the display to emit red, amber or green light. It also contains a bar graph display to indicate the magnitude of the detected signal. A user operable input device in the form of a push button 5 is provided midway up the front of the housing 2 in a position where it can be conveniently operated by a person without having to stoop down. In use, as will be explained hereinafter, the display 4 provides a visible indication of the presence of a magnetic object 6 in proximity of the apparatus as detected by the sensors.

Figure 2:
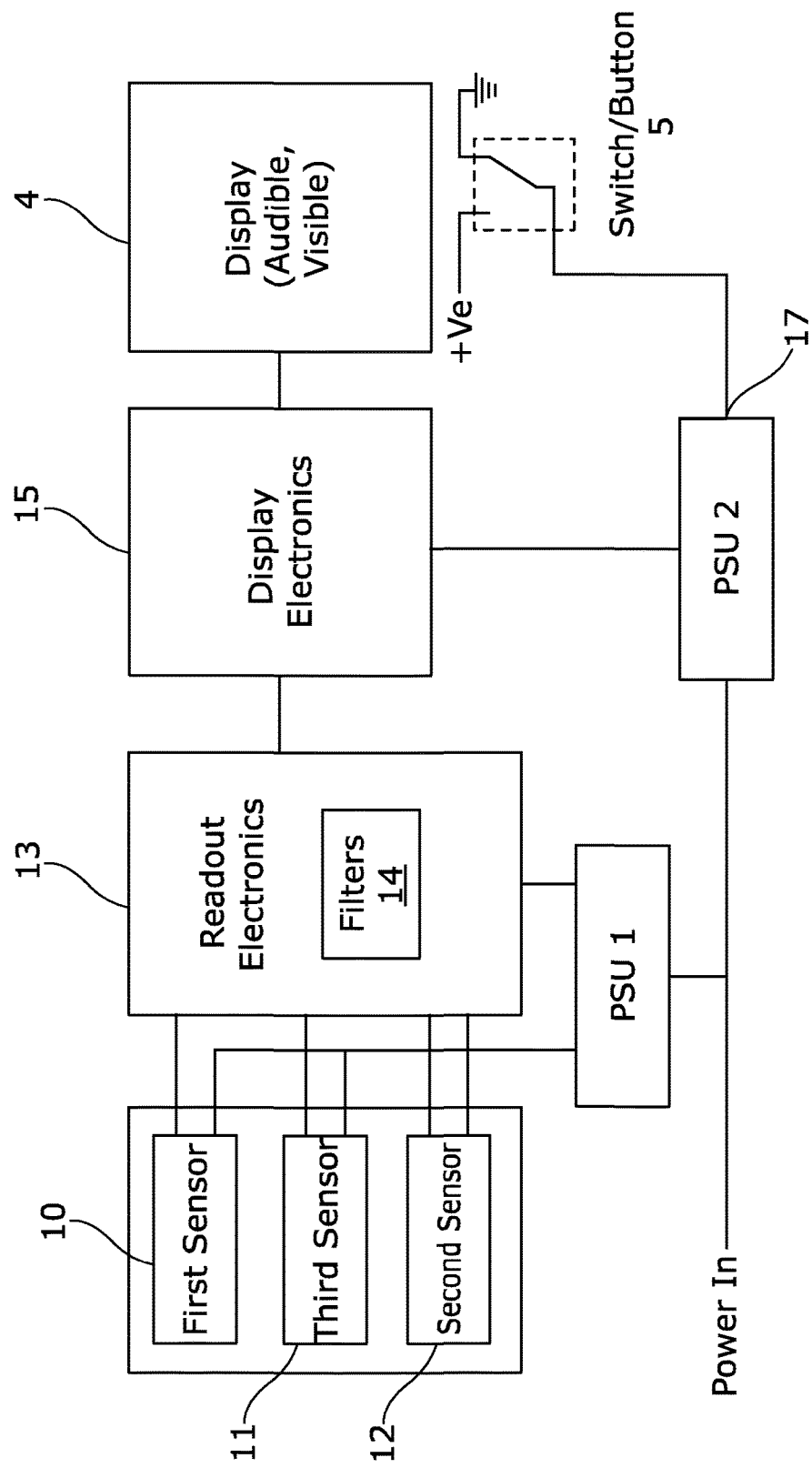
FIG. 2 is a schematic showing the electric circuit of the apparatus of FIG. 1.

In more detail, and with reference to the generalised circuit diagram illustrated in FIG. 2 of the accompanying drawings, the electronic circuit comprises first a main power supply unit PSU 1, which receives incoming power from a remote power supply (not shown but denoted by the phrase "power in"). This may comprise an AC-DC power pack that is located outside of the housing and connects through a power lead and plug to a suitable electrical outlet. The PSU1 converts the incoming power to positive and negative DC voltages of +12v/−12v which are output to positive and negative supply lines in the housing.

Figure 5:
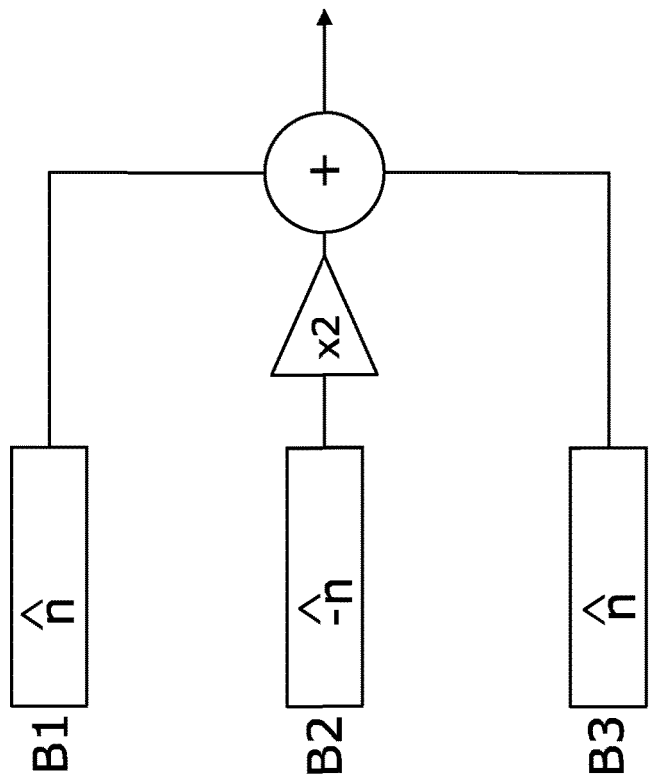
FIG. 5 is an illustration of the arrangement of three sensors of the arrangement of FIG. 1 connected as a second order gradiometer.

Three sensors 10,11,12 are provided in the housing, although in some arrangements there may be only two sensors. The sensors each comprise a sensitive flux gate magnetometer which is sensitive to changes in flux in a localised region of space in the vicinity of the sensor. The sensors are all sensitive over a common overlapping region of space. They are more sensitive to objects very close to the sensor within that space than they are to objects further away in that space. Other types of sensor could be provided, such as magneto-resistive sensors or Hall Effect sensors, or a galvanic coil sensor. Each sensor 10,11,12 outputs a respective measurement signal that is a measurement of the magnetic field incident upon the sensor 10,11,12. The measurement signal from each sensor is passed to a signal processing device forming readout electronics 13. In an alternative arrangement, two sensors could be provided but three are preferred as they can be configured to operate as a second order gradiometer. The configuration required for both the preferred embodiment with three sensors and the alternative with two sensors is illustrated in FIGS. 5 and 4 respectively, where n̂ is a unit vector defining the sensing direction of a sensor and B represents the magnetic field present at the sensor.

Figure 4:
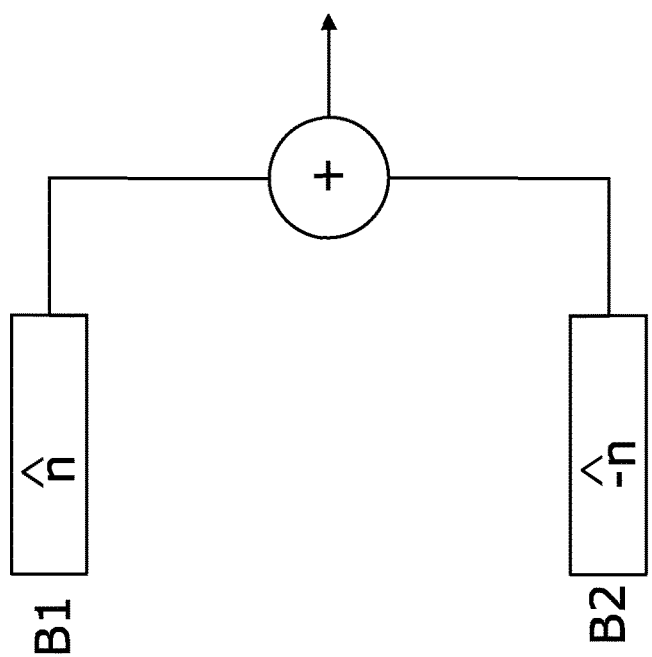
FIG. 4 is an illustration of the arrangement of two sensors in the apparatus of FIG. 1 connected as a first order gradiometer.

With two sensors the sensors are arranged to sense in opposite directions and their outputs are summed as shown in FIG. 4. An alternative would be for the sensors to sense in the same direction and their outputs differenced (not shown) as this is equivalent. In either of these ways they are connected so as to define a first order gradiometer whose output is of the form:

$$\text{Output} \propto (B_1 - B_2) \cdot \hat{n}$$

and if n̂ defines the x direction (extending radially away from the pole) and y defines a baseline extending vertically down through the sensors the output is therefore the first order derivative of the field component of B in the x direction with respect to the y direction, often expressed as $\partial B_x/\partial y$ With the preferred three sensors the sensors are arranged with B1 and B3 sensing in the same direction and B2 sensing in the opposite direction with a relative gain of two with respect to B1 and B3. The outputs are summed as shown in FIG. 5. Alternatively the sensors could all sense in the same direction with B2 given a relative gain of minus-two. With either way the output is of the form:

$$\text{Output} = (B_1 + B_3 - 2B_2) \cdot \hat{n}$$

and if n̂ defines the x direction (extending radially away from the pole) an y defines a baseline extending vertically down through the sensors the output is therefore the second order derivative of the field component of B in the x direction with respect to the y direction, often expressed as $\partial^2 B_x/\partial y^2$, giving a much higher uniformity in the y direction and a much lower sensitivity to distant objects relative to the same object position at a distance compared with the two sensor arrangement.

Since the apparatus will typically be fixed in position when in use for most of the time the sensors 10,11,12 will register a largely unchanging magnetic field due to the earth, and unchanging first and second order gradients. These constitute a large offset on the output of the sensor. This constant offset can be removed using a high pass filter in the readout electronics 13. The sensors will also likely measure regular changes in the magnetic field associated with the power supply for electrical equipment located near the sensors which will cause the output to vary at the supply frequency and its harmonics. This can also be filtered out using a low pass filter in the signal processing device. The filters 14 collectively constitute a band-pass filter 14 to perform these functions. The filtered output of the filters will therefore take a low value, ideally zero, in its steady state.

The sensors and readout electronics receive power from PSU1. Depending on the complexity of the filters 14 that are used there may be a considerable delay between the sensors 10,11,12 and readout electronics being switched on and the filtered output signal settling to a steady state. It is therefore important that the power to the sensors 10,11,12 and the readout electronics 13, at least the filtering stage 14, is kept on at all times when the apparatus might be imminently be needed for pre-screening.

If a ferromagnetic object carried, or pulled or pushed, by a person close to the sensors 10,11,12, the ambient magnetic field will be altered causing a change in the output of the sensor 10,11,12. That change will pass through the filter 14 and be amplified by an amplifier within the readout electronics. In order to trigger an alarm the signal size is compared with a preset threshold. Because the signal may be positive or negative, the threshold (set by a passing the signal through a threshold detector within the readout electronics) consists of a rectification stage followed by a comparator that has a circuit to provide a threshold voltage. Alternatively, separate comparators are used for positive and negative signals with the outputs combined to give a single alarm signal instead of a rectifier and a single comparator. An optional latch (not shown) may be provided which holds the value of the signal output from the comparator for a predetermined period—perhaps up to 1 second.

The output of the comparator is arranged to have logic level zero for the state where the signal does not exceed the threshold, and level 'one' for the state when the signal has exceeded the threshold. Once an object has passed out of range of the sensors 10,11,12 the logic level returns to zero once the signal level has dropped below the threshold. In practice, it may be preferable that the alarm continues for an elapsed time defined by a reset delay and a latch such as a flip-flop that maintains the output at logic one until the switch/button 5 is pressed.

The output of the latch is passed from the readout electronics to an input of the warning device, which comprises a display electronics circuit 15 that drives the display 4. It has been found to be beneficial, although not essential, that both a visual and audible alarm are provided.

In addition the rectified magnetic signal that feeds into the comparator may pass to the warning device to control a bar graph indicator. If the sensors have a digital output or if a digitizer is placed immediately after the sensors then the electronic functions described including the filters, rectifier, comparator, latches and delays may be done with a digital processor rather than in analog electronics.

The warning device 15, 4 is powered from a second power supply PSU2. The power supply PSU2 has an input port 17 which receives a signal from the user operable device and depending on the state of the signal will power up or power down the display electronics. When powered down the display 4 will not issue a warning regardless of the value of the latched signal output from the readout electronics 13. Notably, PSU2 can be powered down without powering down PSU1, so that the warning device can be disabled without cutting power to the sensors 10,11,12 and filters 14.

Figure 3:
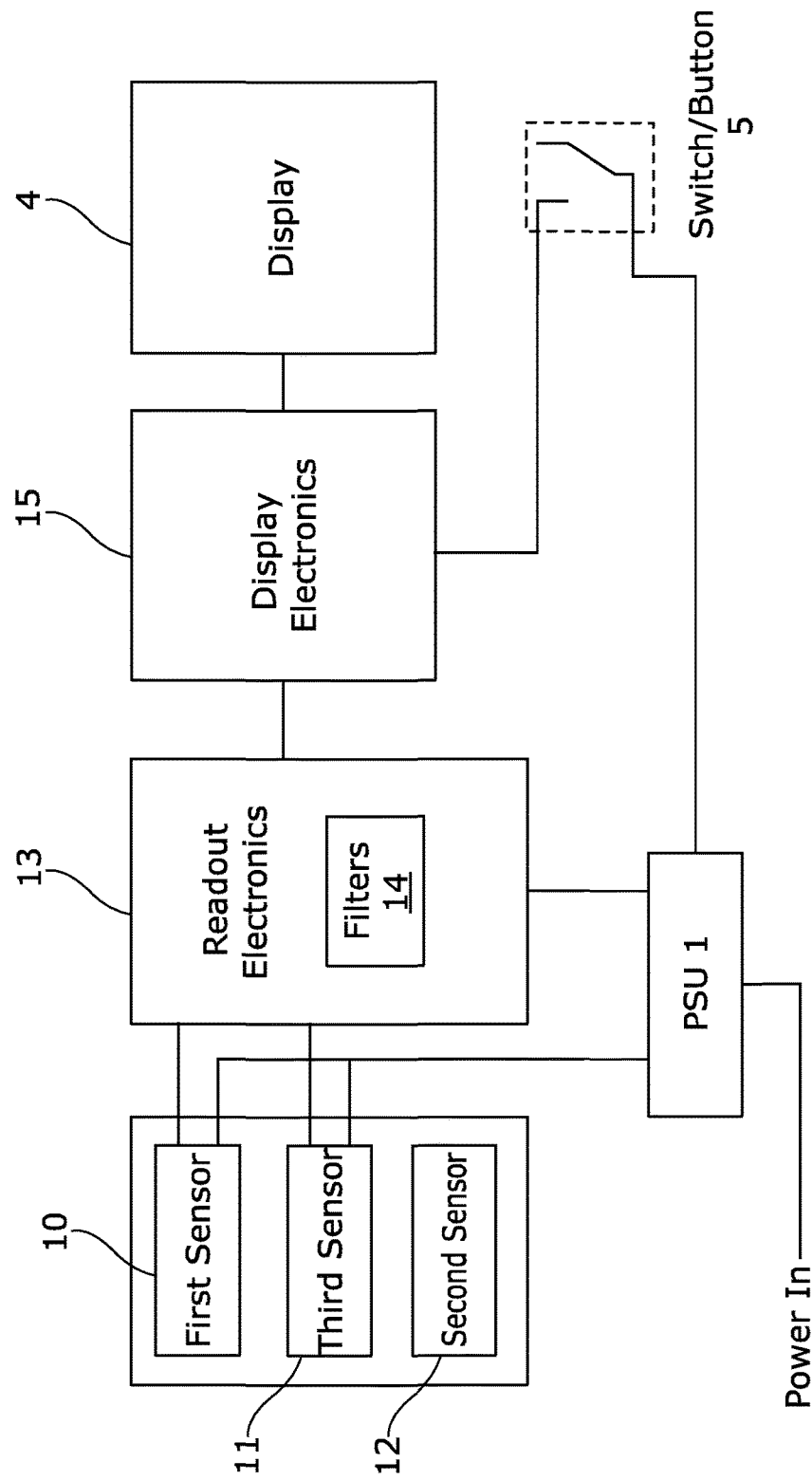
FIG. 3 is a schematic showing an alternative electric circuit of the apparatus of FIG. 1.

A modified electronic circuit which can be used is shown in FIG. 3 of the drawings. Where parts are the same as those used in the circuit of FIG. 2 the same reference numbers have been used for clarity, and the associated description above applies. The key difference is the omission of the second power supply unit PSU2, and the location of the switch 6 in the power supply line from PSU1 to the display electronics. Thus, rather than switching a relatively low current that in turn disables a power supply to the display electronics, the switch breaks the current flowing to the display electronics directly. This has the disadvantage that a break in the power supply line could cause unwanted magnetic fields to be generated unless care is taken during assembly, but does have the benefit of reducing the number and complexity of the components that are needed.

In use, the apparatus may be located at a convenient position in a pre-screening area. A mat 7 is positioned in front of the pole 2, which is in turn oriented so that the user input device faces the mat 7. The apparatus is then connected to a mains electricity supply (unless it contains its own battery power source). As soon as the filters have settled it is ready to use.

Figure 6:
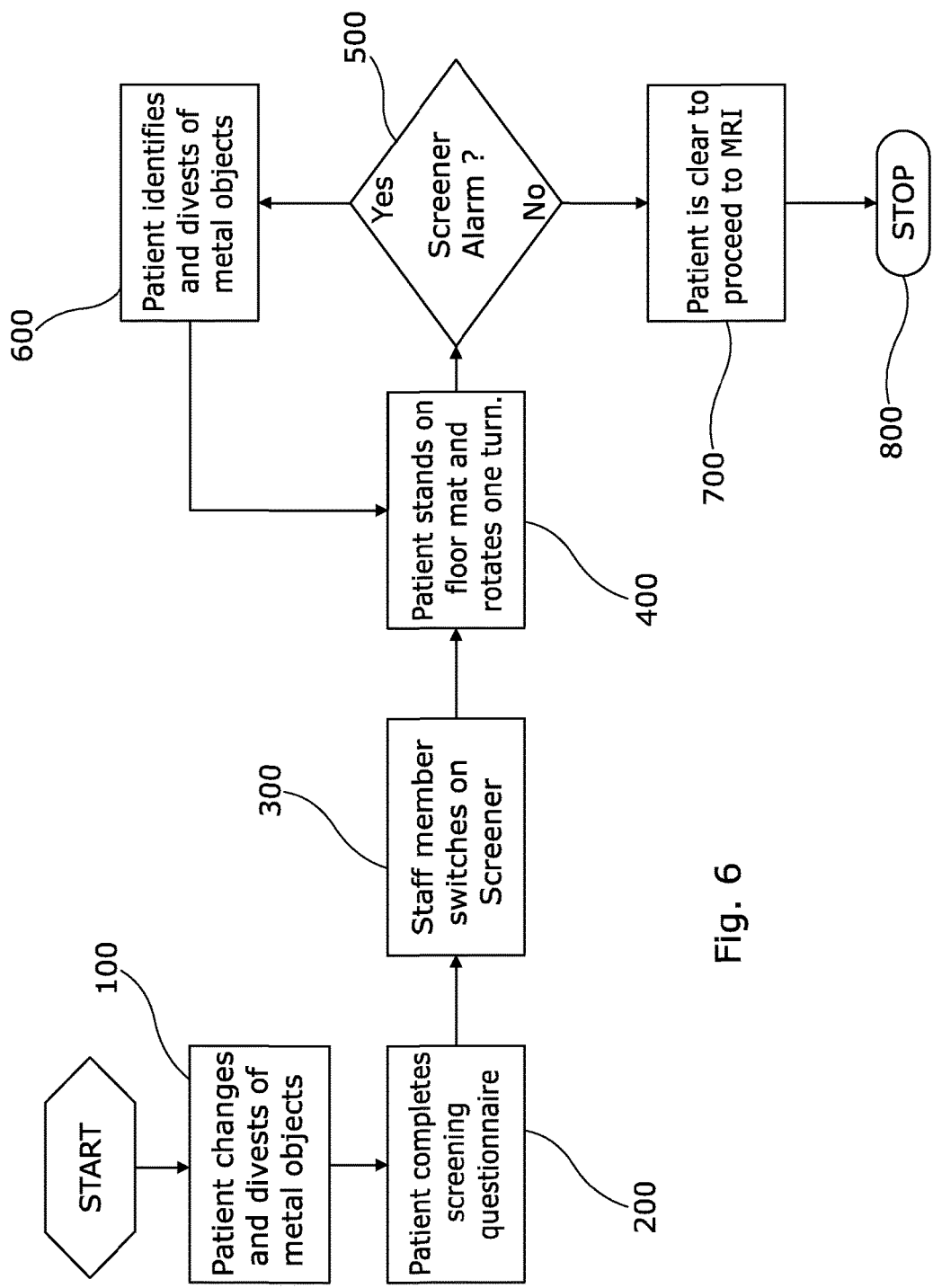
FIG. 6 is a flow chart showing the steps performed when carrying out a method of screening a patient using apparatus of the kind shown in FIG. 1.

A method of using the apparatus to pre-screen a patient is as follows with reference to FIG. 6 of the accompanying drawings:

Initially, before a person is screened a trained MRI person will take that person through a defined pre-screening procedure. First, the patient changes 100 into suitable clothing and removes any metal objects that they may be wearing such as jewellery, hair grips and so on. They are then asked to complete 200 a screening questionnaire which asks for details such as their medical history and whether they have any metal implants such as surgical pins. These preliminary stages may vary from hospital to hospital according to their local procedures so 100 and 200 are by way of example. Once this has been completed to the satisfaction of the trained MRI person, the MRI person will ensure that the warning device is enabled by pressing 300 the button 5 to switch on the screening apparatus. In fact, they are simply turning on the warning device as the apparatus will previously have been switched on so that it settles in its steady state ready for use. It has been found that most times MRI persons prefer the warning display 4 to be disabled, as it otherwise may raise many false alarms as they pass close by and can make them feel that they are being constantly monitored. Furthermore the visual alarm can be distracting when the apparatus is not in use.

After the warning device 4 is enabled, the patient to be screened is invited to stand on the mat 7 in front of the pole with their arms by their side. They will then be asked to rotate 400 through a full circle (360 degrees) whilst remaining standing on the mat 7.

When the person being screened moves onto the mat 7, the presence of ferromagnetic items on or in their body will trigger the warning device because the objects are moving and causing a change in the magnetic field within the overlapping detection zone. Additionally, as the person rotates the objects will trigger 500 the warning device because the magnetic field changes. If the person has a very small ferromagnetic object which is initially hidden from the device because it is positioned, say, on the opposite side of the persons body from the device, it will move closer to the sensors as the person rotates and will trigger the warning device as it moves.

Once the person has rotated through 360 degrees they may then step off the mat. If no alarm was raised they can be cleared 700 to approach an MRI room. If an alarm is raised the person is asked 600 to identify any metal objects and remove them and a more detailed search of their body may be carried out to locate the ferromagnetic object that set off the warning device. The step of rotating the person in front of the apparatus is then repeated until no warning sound is issued. The patient is then deemed safe to proceed 700 to the MRI scanner room and the method of pre-screening ends 800.

A modified step 400 is required if the patient is non-ambulatory. In this case the patient would be screened in a non-magnetic portering chair, wheelchair or gurney (known as transfer equipment). Then the patient is pushed over the mat 7 in one direction and then rotated through one half turn (180 degrees) and pushed back past the apparatus over mat 7 so the other side of the patient is also scanned. This requires the MRI person to be free of ferromagnetic material so that neither the person or the transfer equipment cause an alarm.

This method may be used to determine whether an object of unknown composition contains ferromagnetic material prior to being taken into an MRI room. Examples of items that could be tested are cylinders, patient monitoring equipment, tools, cleaning equipment, or anything where there is uncertainty as to whether it would be safe or a potential projectile effect hazard.

The invention claimed is:

1. Apparatus for detecting a ferromagnetic object located on or in a person being screened, the apparatus comprising:
   at least a first magnetic sensor which in use measures an ambient magnetic field or gradient within a first volume of space and produces a corresponding measurement signal,
   a primary power supply which provides power to the at least first magnetic sensor,
   a signal processing circuit arranged in communication with the at least first magnetic sensor configured to identify temporal variations in the measurement signal and from the identified temporal variations provide an output signal indicative of the presence of a ferromagnetic object within the volume of space,
   and
   a warning device operable by the output from the signal processing circuit to provide within a vicinity the apparatus at least one of an audible and a visible warning in response to the output signal from the signal processing circuit,
   wherein the apparatus includes a user operable input device which enables the warning device to be disabled by a user without powering down the at least first magnetic sensor.

2. The apparatus according to claim 1 in which the signal processing circuit includes one or more filters and in which the output signal from the at least first magnetic sensor is passed through at least one of the filters.

3. The apparatus according to claim 2 in which the user operable input device enables the warning device to be disabled without powering down the filters.

4. The apparatus according to claim 1 in which the user operable input device alters the value of a relatively low current electrical signal, the apparatus disabling or enabling the warning device according to the value of that signal.

5. The apparatus according to claim 4 in which the signal is carried from the user operable input device along twisted pair cables.

6. The apparatus according to claim 4 which includes a second power supply which provides an output power for the warning device, the output of the second power supply being switchable between a level at which the power to the warning device is enabled and a level at which power to the warning device is disabled, the condition of the output being dependent on the value of the signal from the user operable input device.

7. The apparatus according to claim 1 in which the output of the primary power supply is connected to the signal processing circuit and warning device through a twisted pair cable.

8. The apparatus according to claim 1 which comprises a single housing within which the signal processing circuit, the at least first magnetic sensor, and power supply are located.

9. The apparatus according to claim 8 whereby when in a position of use the user operable input device is located on the housing at a height where it can be pressed by a user of average height without having to stoop down.

10. The apparatus according to claim 8 which includes a mat which in use is positioned on the ground in front of the housing and which indicates where a person must stand to be within the volume of space.

11. The apparatus according to claim 8 which the housing comprises a pole, the at least first magnetic sensor is located at or close to the top of the pole, and a second magnetic sensor is located at or close to the bottom of the pole, and the user operable input device is located conveniently at or close to the midpoint of the pole.

12. The apparatus according to claim 1 in which the user operable input device comprises a button or a switch.

13. The apparatus according to claim 1 which further includes a second magnetic sensor which in use measures an ambient magnetic field or gradient within a second volume of space that at least partially overlaps the first volume of space and produces a corresponding measurement signal and in which the signal processing circuit is configured such that the first and second sensors are configured as a gradiometer.

14. The apparatus according to claim 13 which includes a third sensor and the first, second and third sensors are configured as a second order gradiometer.

15. A method of screening a person or object comprising:
providing an apparatus comprising at least a first magnetic sensor which in use measures an ambient magnetic field or gradient within a first volume of space that is sufficient to encompass an entire body of a person and produces a corresponding measurement signal,
a primary power supply which provides power to the at least first magnetic sensor,
a signal processing circuit arranged in communication with the at least first magnetic sensor configured to identify temporal variations in the measurement signal and from the identified temporal variations provide an output signal indicative of a presence of a ferromagnetic object within the first volume of space,
and a warning device operable by the output from the signal processing circuit to provide within the vicinity the apparatus at least one of an audible and a visible warning in response to the output signal from the signal processing circuit,
the method comprising the steps of:
(a) positioning an entire body of the person or object to be screened within the first volume of space in a first orientation,
(b) rotating the entire body of the person or object in the first volume of space through 180 degrees from the first orientation to a second orientation, and
(c) observing any warning from the warning device.

16. The method of claim 15 in which the step of rotating the entire body of the person or object comprises rotating them when they are positioned in the volume of space.

17. The method of claim 16 in which the step of rotating the entire body of the person or object comprises rotating the patient through 360 degrees within the volume of space.

18. The method of claim 16 which includes providing a mat and positioning the person or object on the mat, and rotating the person or object remains standing on the mat, the mat being positioned below the volume of space, and preferably wholly within the zone.

19. The method of claim 15 in which the apparatus includes a user operable input device which permits the warning device to be disabled without powering down the at least first magnetic sensor and the method comprises an additional step (d) of powering up the display using the user operable input device.

20. The method of claim 19 which further comprises upon completion disabling the display without powering down the at least first magnetic sensor or signal processing circuit using the user operable input device.

21. The method of claim 15 which includes a step of introducing a magnetic object in front of the warning device after the display is powered up to test the display prior to positioning the entire body of the person or object.

22. The method of claim 15 whereby the person or object is carried in a non: ferromagnetic transfer equipment past the apparatus first in one direction and then in the opposite direction in both cases close to the apparatus such that both sides of the person or object are scanned.

23. Apparatus for detecting a ferromagnetic object located on or in a person being screened, the apparatus comprising:
at least a first magnetic sensor which in use measures an ambient magnetic field or gradient within a first volume of space and produces a corresponding measurement signal,
a primary power supply which provides power to the at least first magnetic sensor,
a signal processing circuit arranged in communication with the at least first magnetic sensor configured to identify temporal variations in the measurement signal and from the identified temporal variations provide an output signal indicative of the presence of a ferromagnetic object within the volume of space,
and
a warning device operable by the output from the signal processing circuit to provide within the vicinity the apparatus at least one of an audible and a visible warning in response to the output signal from the signal processing circuit, wherein the apparatus includes a user operable input device which enables the warning device to be disabled by a user without powering down the at least first magnetic sensor.

* * * * *

UNITED STATES PATENT AND TRADEMARK OFFICE
CERTIFICATE OF CORRECTION

PATENT NO. : 9,995,713 B2
APPLICATION NO. : 14/129877
DATED : June 12, 2018
INVENTOR(S) : S. W. Goodyear et al.

Page 1 of 1

It is certified that error appears in the above-identified patent and that said Letters Patent is hereby corrected as shown below:

In the Claims

| Column | Line | Error |
|---|---|---|
| 12 (Claim 22 Line 2) | 25 | "non: ferromagnetic" should read --non-ferromagnetic-- |

Signed and Sealed this
Twentieth Day of November, 2018

Andrei Iancu
*Director of the United States Patent and Trademark Office*